(12) United States Patent
Stenzler

(10) Patent No.: US 6,793,644 B2
(45) Date of Patent: Sep. 21, 2004

(54) DEVICE AND METHOD FOR TREATMENT OF SURFACE INFECTIONS WITH NITRIC OXIDE

(75) Inventor: Alex Stenzler, Orange, CA (US)

(73) Assignee: Sensormedics Corporation, Yorba Linda, CA (US)

( * ) Notice: Subject to any disclaimer, the term of this patent is extended or adjusted under 35 U.S.C. 154(b) by 0 days.

(21) Appl. No.: 10/172,270

(22) Filed: Jun. 14, 2002

(65) Prior Publication Data

US 2002/0156416 A1 Oct. 24, 2002

Related U.S. Application Data

(63) Continuation of application No. 09/749,022, filed on Dec. 26, 2000, now Pat. No. 6,432,077.

(51) Int. Cl.[7] .................. A61M 37/00; A01N 59/02
(52) U.S. Cl. ............... 604/23; 604/290; 424/718
(58) Field of Search ................ 604/289, 290, 604/25, 23; 424/718

(56) References Cited

U.S. PATENT DOCUMENTS

| | | | | |
|---|---|---|---|---|
| 3,192,106 | A | * 6/1965 | Bracken et al. | 424/43 |
| 4,224,941 | A | 9/1980 | Stivala | 604/23 |
| 4,608,041 | A | 8/1986 | Nielsen | 604/23 |
| 5,427,797 | A | 6/1995 | Frostell et al. | 424/434 |
| 5,519,020 | A | 5/1996 | Smith et al. | 424/718 |
| 5,632,981 | A | 5/1997 | Saavedra et al. | 424/78.08 |
| 5,810,795 | A | * 9/1998 | Westwood | 604/305 |
| 5,814,666 | A | 9/1998 | Green et al. | 514/611 |
| 5,845,633 | A | 12/1998 | Psaros | 128/200.24 |
| 5,918,596 | A | 7/1999 | Heinonen | 128/204.21 |
| 6,103,275 | A | * 8/2000 | Seitz et al. | 424/718 |
| 6,131,572 | A | * 10/2000 | Heinonen | 128/205.24 |
| 6,160,021 | A | 12/2000 | Lerner et al. | 514/645 |
| 6,432,077 | B1 | * 8/2002 | Stenzler | 604/23 |
| 2002/0155164 | A1 | * 10/2002 | Figley et al. | 424/600 |

FOREIGN PATENT DOCUMENTS

| | | | |
|---|---|---|---|
| EP | 0659445 A1 | 6/1995 | A61M/16/00 |
| EP | 0659445 B1 | 6/1995 | A61M/16/00 |
| FR | 2656218 | 6/1991 | A61F/13/00 |
| WO | WO 93/17741 | 9/1993 | A61M/11/00 |
| WO | WO 95/09612 | 4/1995 | A61K/9/127 |
| WO | WO 96/00006 | 1/1996 | A01N/43/04 |
| WO | WO 96/22803 | 8/1996 | A61M/16/12 |
| WO | WO 96/25184 | 8/1996 | A61L/9/04 |
| WO | WO 96/31217 | 10/1996 | A61K/31/675 |
| WO | WO 98/01142 | 1/1998 | A61K/33/00 |
| WO | WO 00/30659 | 6/2000 | A61K/33/08 |

OTHER PUBLICATIONS

Hoehn et al., Effect of Therapeutic Concentrations of Nitric Oxide on Bacterial Grown in vitro, Crit Care Med, vol. 26, No. 11, pp. 1857–1862(1998).

Long et al., Mycobacteriocidal Action of Exogenous Nitric Oxide, Antimicrobial Agents and Chemotherapy, vol. 43, No., pp. 403–405 (Feb. 1999).

Mancinelli et al., Effects of Nitric Oxide and Nitrogen Dioxide on Bacterial Growth, Applied and Environmental Microbiology, vol. 46, No. 1, pp. 198–202 (Jul. 1983).

Webert et al., Effects of Inhaled Nitric Oxide In A Rat Model of *Pseudomonas ceruginosa* Pneumonia, Crit Car Med, vol. 28, No. 7, pp. 2397–2405 (2000).

* cited by examiner

*Primary Examiner*—John J. Calvert
*Assistant Examiner*—Linh Truong
(74) *Attorney, Agent, or Firm*—Sidley Austin Brown & Wood LLP

(57) ABSTRACT

A method of treating infected tissue with topical nitric oxide exposure includes the steps of providing a source of nitric oxide containing gas and delivering the nitric oxide containing gas to a skin surface containing infected tissue so as to bathe the infected tissue with nitric oxide.

23 Claims, 3 Drawing Sheets

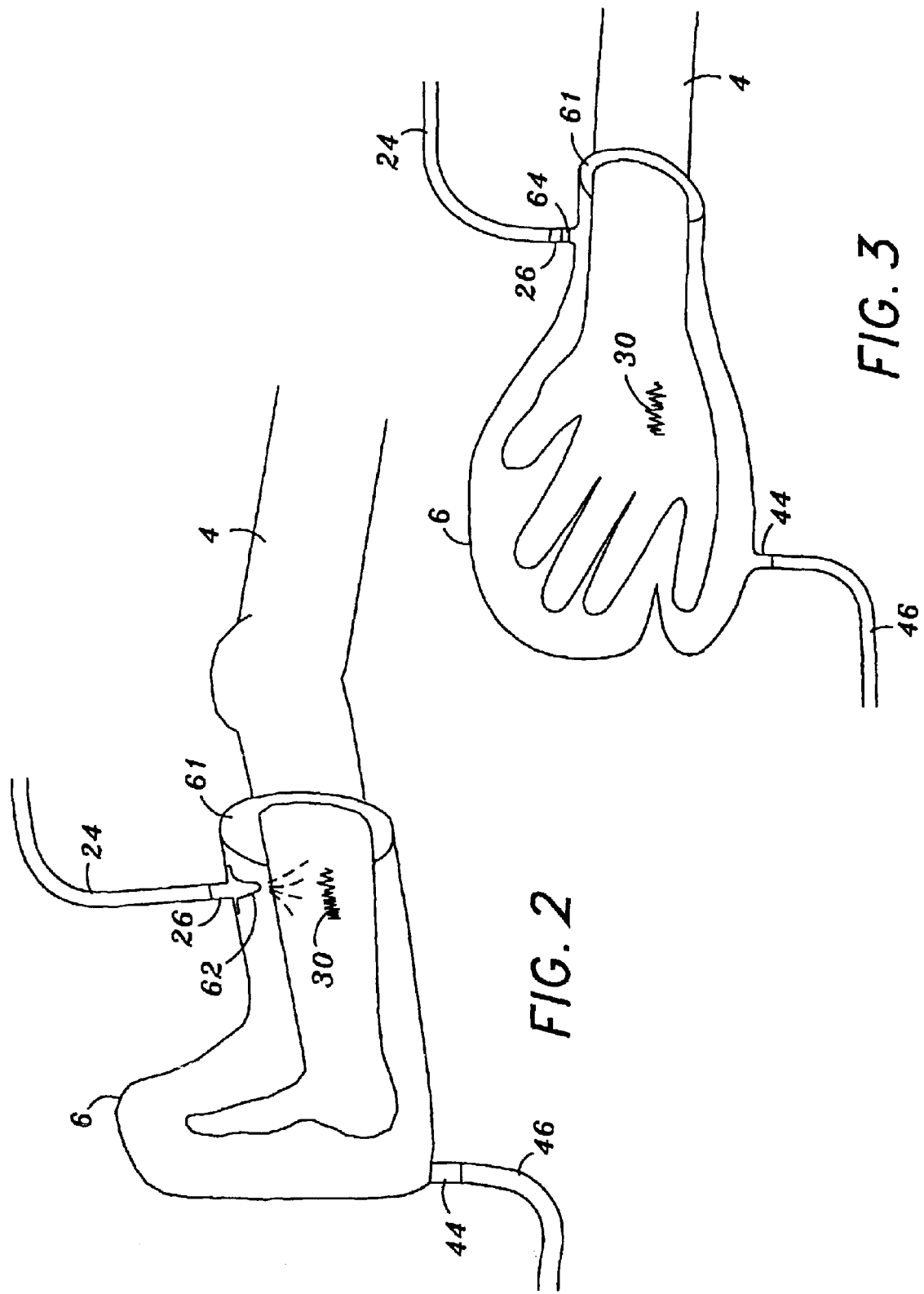

DEVICE AND METHOD FOR TREATMENT OF SURFACE INFECTIONS WITH NITRIC OXIDE

This Application is a continuation of U.S. application Ser. No. 09/749,022, filed on Dec. 26, 2000, now U.S. Pat. No. 6,432,077. The '022 application is incorporated by reference as if set forth fully herein.

FIELD OF THE INVENTION

The field of the invention relates devices and methods for treating infected tissue. More specifically, the invention relates to devices and methods for treating surface and subsurface infections with topical nitric oxide exposure.

BACKGROUND OF THE INVENTION

The treatment of infected surface or subsurface lesions in patients has typically involved the topical or systemic administration of anti-infective agents to a patient. Antibiotics are one such class of anti-infective agents that are commonly used to treat an infected abscess, lesion, wound, or the like. Unfortunately, an increasingly number of infective agents such as bacteria have become resistant to conventional antibiotic therapy. Indeed, the increased use of antibiotics by the medical community has led to a commensurate increase in resistant strains of bacteria that do not respond to traditional or even newly developed anti-bacterial agents. Even when new anti-infective agents are developed, these agents are extremely expensive and available only to a limited patient population.

Another problem with conventional anti-infective agents is that some patients are allergic to the very compounds necessary to their treat their infection. For these patients, only few drugs might be available to treat the infection. If the patient is infected with a strain of bacteria that does not respond well to substitute therapies, the patient's life can be in danger.

A separate problem related to conventional treatment of surface or subsurface infections is that the infective agent interferes with the circulation of blood within the infected region. It is sometimes the case that the infective agent causes constriction of the capillaries or other small blood vessels in the infected region which reduces bloodflow. When bloodflow is reduced, a lower level of anti-infective agent can be delivered to the infected region. In addition, the infection can take a much longer time to heal when bloodflow is restricted to the infected area. This increases the total amount of drug that must be administered to the patient, thereby increasing the cost of using such drugs. Topical agents may sometimes be applied over the infected region. However, topical anti-infective agents do not penetrate deep within the skin where a significant portion of the bacteria often reside. Topical treatments of anti-infective agents are often less effective at eliminating infection than systemic administration (i.e., oral administration) of an anti-infective pharmaceutical.

In the 1980's, it was discovered by researchers that the endothelium tissue of the human body produced nitric oxide (NO), and that NO is an endogenous vasodilator, namely, and agent that widens the internal diameter of blood vessels. NO is most commonly known as an environmental pollutant that is produced as a byproduct of combustion. At high concentrations, NO is toxic to humans. At low concentrations, researchers have discovered that inhaled NO can be used to treat various pulmonary diseases in patients. For example, NO has been investigated for the treatment of patients with increased airway resistance as a result of emphysema, chronic bronchitis, asthma, adult respiratory distress syndrome (ARDS), and chronic obstructive pulmonary disease (COPD).

NO has also been investigated for its use as a sterilizing agent. It has been discovered that NO will interfere with or kill the growth of bacteria grown in vitro. PCT International Application No. PCT/CA99/01123 published Jun. 2, 2000 discloses a method and apparatus for the treatment of respiratory infections by NO inhalation. NO has been found to have either an inhibitory and/or a cidal effect on pathogenic cells.

While NO has shown promise with respect to certain medical applications, delivery methods and devices must cope with certain problems inherent with gaseous NO delivery. First, exposure to high concentrations of NO is toxic, especially exposure to NO in concentrations over 1000 ppm. Even lower levels of NO, however, can be harmful if the time of exposure is relatively high. For example, the Occupational Safety and Health Administration (OSHA) has set exposure limits for NO in the workplace at 25 ppm timeweighted averaged for eight (8) hours. It is extremely important that any device or system for delivering NO include features that prevent the leaking of NO into the surrounding environment. If the device is used within a closed space, such as a hospital room or at home, dangerously high levels of NO can build up in a short period of time.

Another problem with the delivery of NO is that NO rapidly oxidizes in the presence of oxygen to form $NO_2$, which is highly toxic, even at low levels. If the delivery device contains a leak, unacceptably high levels of $NO_2$ gas can develop. In addition, to the extent that NO oxidizes to form $NO_2$, there is less NO available for the desired therapeutic effect. The rate of oxidation of NO to $NO_2$ is dependent on numerous factors, including the concentration of NO, the concentration of $O_2$, and the time available for reaction. Since NO will react with the oxygen in the air to convert to $NO_2$, it is desirable to have minimal contact between the NO gas and the outside environment.

Accordingly, there is a need for a device and method for the treatment of surface and subsurface infections by the topical application of NO. The device is preferably leak proof to the largest extent possible to avoid a dangerous build up of NO and $NO_2$ concentrations. In addition, the device should deliver NO to the infected region of the patient without allowing the introduction of air that would otherwise react with NO to produce $NO_2$. The application of NO to the infected region preferably decreases the time required to heal the infected area by reducing pathogen levels. The device preferably includes a NO and $NO_2$ absorber or scrubber that will remove or chemically alter NO and $NO_2$ prior to discharge of the air from the delivery device.

SUMMARY OF THE INVENTION

In a first aspect of the invention, a device for the topical delivery of nitric oxide gas to an infected area of skin includes a source of nitric oxide gas, a bathing unit, a flow control valve, and a vacuum unit. The bathing unit is in fluid communication with the source of nitric oxide gas and is adapted for surrounding the area of infected skin and forming a substantially air-tight seal with the skin surface. The flow control valve is positioned downstream of the source of nitric oxide and upstream of the bathing unit for controlling the amount of nitric oxide gas that is delivered to the bathing unit. The vacuum unit is positioned downstream of the bathing unit for withdrawing gas from the bathing unit.

In a second aspect of the invention, the device according to the first aspect of the invention includes a controller for controlling the operation of the flow control valve and the vacuum unit.

In a third aspect of the invention, the device according to the first aspect of the invention further includes a source of dilutent gas and a gas blender. The dilutent gas and the nitric oxide gas are mixed by the gas blender. The device also includes a nitric oxide gas absorber unit that is positioned upstream of the vacuum unit. The device also includes a controller for controlling the operation of the flow control valve and the vacuum unit.

In a fourth aspect of the invention, a method of delivering an effective amount of nitric oxide to an infected area of skin includes the steps of providing a bathing unit around the infected area of skin, the bathing unit forming a substantially air-tight seal with the skin. Gas containing nitric oxide is then transported to the bathing unit so as to bathe the infected area of skin with gaseous nitric oxide. Finally, at least a portion of the nitric oxide gas is evacuated from the bathing unit.

In a fifth aspect of the invention a method of treating infected tissue with topical nitric oxide exposure includes the steps of providing a source of nitric oxide containing gas and delivering the nitric oxide containing gas to a skin surface containing infected tissue so as to bathe the infected tissue with nitric oxide.

It is an object of the invention to provide a delivery device for the topical delivery of a NO-containing gas to an infected area of skin. It is a further object of the device to prevent the NO-containing gas from leaking from the delivery device. The method of delivering an effective amount of nitric oxide gas to the infected area of skin kills bacteria and other pathogens and promotes the healing process.

BRIEF DESCRIPTION OF THE DRAWINGS

FIG. 2 illustrates a bathing unit surrounding the foot of a patient.

FIG. 3 illustrates a bathing unit surrounding the hand of a patient.

DETAILED DESCRIPTION OF THE PREFERRED EMBODIMENTS

Figure 1:
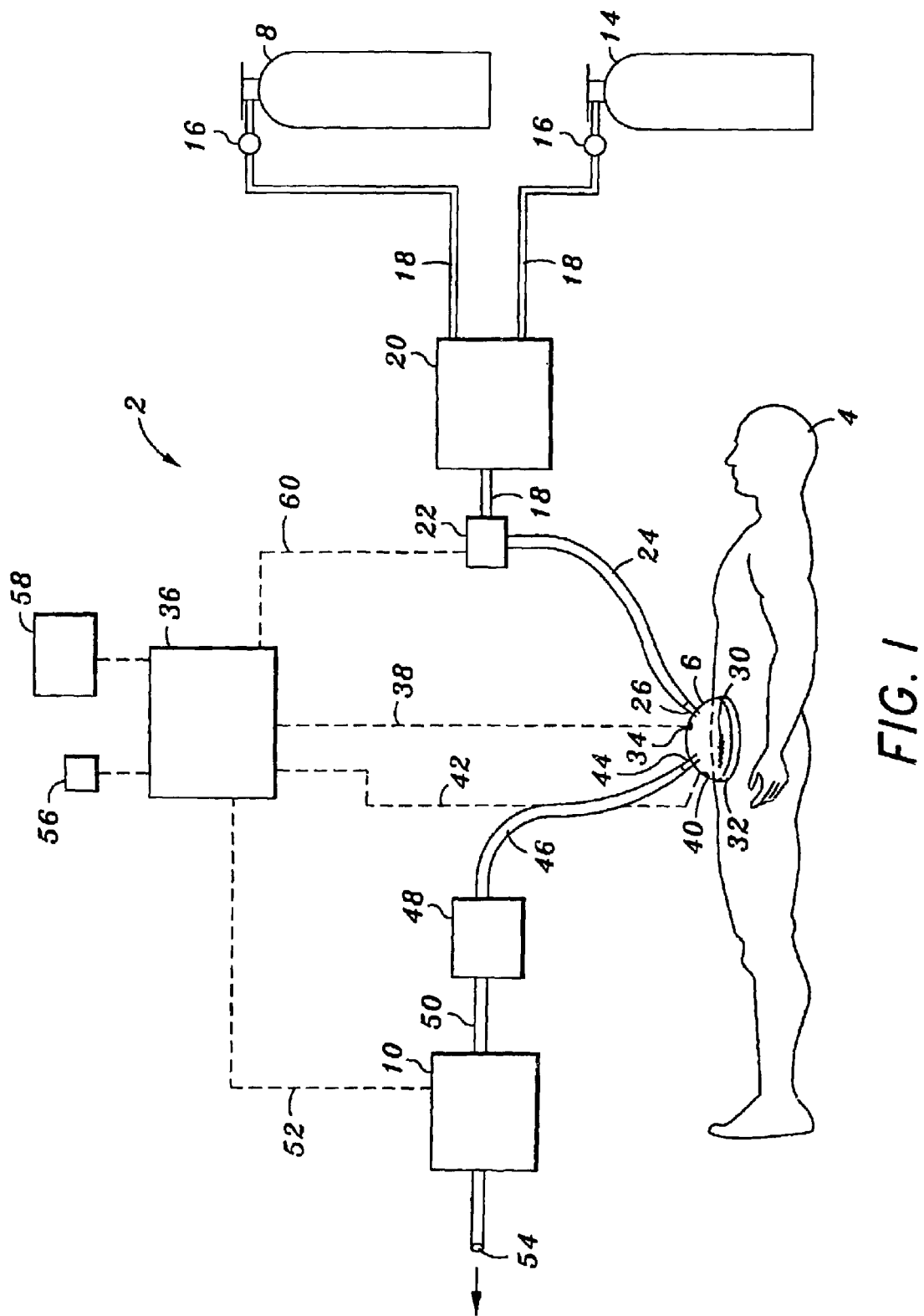
FIG. 1 illustrates a schematic representation of the NO delivery device according to one aspect of the invention.

Referring now to FIG. 1, a NO delivery device 2 is shown connected to a patient 4. In its most general sense, the NO delivery device 2 includes a bathing unit 6 that is fluidically connected to a NO gas source 8, a flow control valve 22, and a vacuum unit 10. FIG. 1 illustrates one preferred embodiment of the invention.

In FIG. 1, the NO gas source 8 is a pressurized cylinder containing NO gas. While the use of a pressurized cylinder is the preferred method of storing the NO-containing gas source 8, other storage and delivery means, such as a dedicated feed line (wall supply) can also be used. Typically, the NO gas source 8 is a mixture of $N_2$ and NO. While $N_2$ is typically used to dilute the concentration of NO within the pressurized cylinder, any inert gas can also be used. When the NO gas source 8 is stored in a pressurized cylinder, it is preferable that the concentration of NO in the pressurized cylinder fall within the range of about 800 ppm to about 1200 ppm. Commercial nitric oxide manufacturers typically produce nitric oxide mixtures for medical use at around the 1000 ppm range. Extremely high concentrations of NO are undesirable because accidental leakage of NO gas is more hazardous, and high partial pressures of NO tends to cause the spontaneous degradation of NO into nitrogen dioxide. Pressurized cylinders containing low concentrations of NO (i.e., less than 100 ppm NO) can also be used in accordance the device and method disclosed herein. Of course, the lower the concentration of NO used, the more often the pressurized cylinders will need replacement.

FIG. 1 also shows source of dilutent gas 14 as part of the NO delivery device 2 that is used to dilute the concentration of NO. The source of dilutent gas 14 can contain $N_2$, $O_2$, Air, an inert gas, or a mixture of these gases. It is preferable to use a gas such as $N_2$ or an inert gas to dilute the NO concentration since these gases will not oxidize the NO into $NO_2$ as would $O_2$ or air. The source of dilutent gas 14 is shown as being stored within a pressurized cylinder. While the use of a pressurized cylinder is shown in FIG. 1 as the means for storing the source of dilutent gas 14, other storage and delivery means, such as a dedicated feed line (wall supply) can also be used.

The NO gas from the NO gas source 8 and the dilutent gas from the dilutent gas source 14 preferably pass through pressure regulators 16 to reduce the pressure of gas that is admitted to the NO delivery device 2. The respective gas streams pass via tubing 18 to an optional gas blender 20. The gas blender 20 mixes the NO gas and the dilutent gas to produce a NO-containing gas that has a reduced concentration of NO. Preferably, the NO-containing gas that is output from the gas blender 20 has a concentration that is less than about 200 ppm. Even more preferably, the concentration of NO-containing gas that is output from the gas blender 20 is less than about 100 ppm.

The NO-containing gas that is output from the gas blender 20 travels via tubing 18 to a flow control valve 22. The flow control valve 22 can include, for example, a proportional control valve that opens (or closes) in a progressively increasing (or decreasing if closing) manner. As another example, the flow control valve 22 can include a mass flow controller. The flow control valve 22 controls the flow rate of the NO-containing gas that is input to the bathing unit 6. The NO-containing gas leaves the flow control valve 22 via flexible tubing 24. The flexible tubing 24 attaches to an inlet 26 in the bathing unit 6. The inlet 26 might include an optional one way valve 64 (see FIG. 3) that prevents the backflow of gas into the tubing 24.

Still referring to FIG. 1, the bathing unit 6 is shown sealed against the skin surface of a patient 4. The infected area 30 which can be an abscess, lesion, wound, or the like, is enclosed by the bathing unit 6. The bathing unit 6 preferably includes a seal portion 32 that forms a substantially air-tight seal with the skin of the patient 4. Substantially air-tight is meant to indicate that the NO-containing gas does not leak out of the bathing unit 6 in significant amounts (i.e., no more than about 5% of the NO-containing gas delivered to the bathing unit 6). The seal portion 32 may comprise an inflatable seal 61, such as that shown in FIGS. 2 and 3, or alternatively the seal portion 32 may comprise a flexible skirt or the like that confirms to the surface of the patient 4. The seal portion 32 also might include an adhesive portion that adheres to the skin surface of a patient 4. In other envisioned embodiments, the sealing portion 32 may merely comprise the interface of the bathing unit 6 with the surface of the patient's 4 skin.

The bathing unit 6 can be made of a virtually limitless number of shapes and materials depending on its intended use. The bathing unit 6 might be formed as a rigid structure, such as that shown in FIG. 1, that is placed over the infected area 30. Alternatively, the bathing unit 6 can be formed of a flexible, baglike material that is inflatable over the infected area 30. FIG. 2 shows such a structure in the shape of a boot that is placed over the patient's 4 foot. FIG. 3 shows another inflatable bathing unit 6 that is formed in the shape of a mitten or glove that is worn over the patient's 4 hand.

In one preferred embodiment of the invention, the bathing unit 6 includes an NO sensor 34 that measures the concentration of NO gas within the bathing unit 6. The NO sensor 34 preferably reports this information to a controller 36 via signal line 38. An optional $NO_2$ sensor 40 can also be included within the bathing unit 6. The $NO_2$ sensor 40 preferably reports the concentration of $NO_2$ to the controller 36 via signal line 42. The sensors 40, 42 can be a chemilluminesense-type, electrochemical cell-type, or spectrophotometric-type sensor.

The bathing unit 6 also includes an outlet 44 that is used to remove gas from the bathing unit 6. The outlet 44 is preferably located away from the gas inlet 26 such that NO gas does not quickly enter and exit the bathing unit 6. Preferably, the inlet 26 and outlet 44 are located in areas of the bathing unit 6 such that the NO gas has a relatively long residence time. Flexible tubing 46 is connected to the outlet 44 and provides a conduit for the removal of gases from the bathing unit 6.

In one preferred embodiment of the invention, the flexible tubing 46 is in fluid communication with an absorber unit 48. The absorber unit 48 preferably absorbs or strips NO from the gas stream that is exhausted from the bathing unit 6. It is also preferable for the absorber unit 48 to also absorb or strip $NO_2$ from the gas stream that is exhausted from the bathing unit 6. Since these gases are toxic at high levels, it is preferable that these components are removed from the delivery device 2 prior to the gas being vented to the atmosphere. In addition, these gases can react with the internal components of the vacuum unit 10 and interfere with the operation of the delivery device 2.

The now clean gas travels from the absorbing unit 48 to the vacuum unit 10 via tubing 50. The vacuum unit 10 provides a negative pressure within the tubing 50 so as to extract gases from the bathing unit 6. The vacuum unit 10 is preferably controllable with respect to the level of vacuum or suction supplied to the tubing 50 and bathing unit 6. In this regard, in conjunction with the flow control valve 22, the amount of NO gas within the bathing unit 6 can be regulated. Preferably, the vacuum unit 10 is coupled with the controller 36 via a signal line 52. The controller 36, as discussed below, preferably controls the level of output of the vacuum unit 10. The gas then passes from the vacuum unit 10 to a vent 54 that is open to the atmosphere.

It should be understood that the absorbing unit 48 is an optional component of the delivery device 2. The gas laden with NO and $NO_2$ does not have to be removed from the gas stream if there is no concern with local levels of NO and $NO_2$. For example, the gas can be exhausted to the outside environment where high concentrations of NO and $NO_2$ will not develop. Alternatively, a recirculation system (not shown) might be used to recycle NO with the bathing unit 6.

Still referring to FIG. 1, the delivery device 2 preferably includes a controller 36 that is capable of controlling the flow control valve 22 and the vacuum unit 10. The controller 36 is preferably a microprocessor-based controller 36 that is connected to an input device 56. The input device 56 is used by an operator to adjust various parameters of the delivery device such as NO concentration, residence time of NO, pressure within the bathing unit 6, etc. An optional display 58 can also be connected with the controller 36 to display measured parameters and settings such as the set-point NO concentration, the concentration of NO within the bathing unit 6, the concentration of $NO_2$ within the bathing unit 6, the flow rate of gas into the bathing unit 6, the flow rate of gas out of the bathing unit 6, the total time of delivery, and the like.

The controller 36 preferably receives signals from sensors 34, 40 regarding gas concentrations if such sensors 34, 40 are present within the delivery device 2. Signal lines 60, 52 are connected to the flow control valve 22 and vacuum unit 10 respectively for the delivery and receipt of control signals.

In another embodiment of the invention, the controller 36 is eliminated entirely. In this regard, the flow rate of the gas into the bathing unit 6 and the flow rate of the gas out of the bathing unit 6 are pre-set or adjusted manually. For example, an operator can set a vacuum output that is substantially equal to the flow rate of the gas delivered to the bathing unit 6 via the flow control valve 22. In this manner, NO gas will be able to bathe the infected area 30 without any build-up or leaking of NO or $NO_2$ gas from the delivery device 2.

Figure 4:
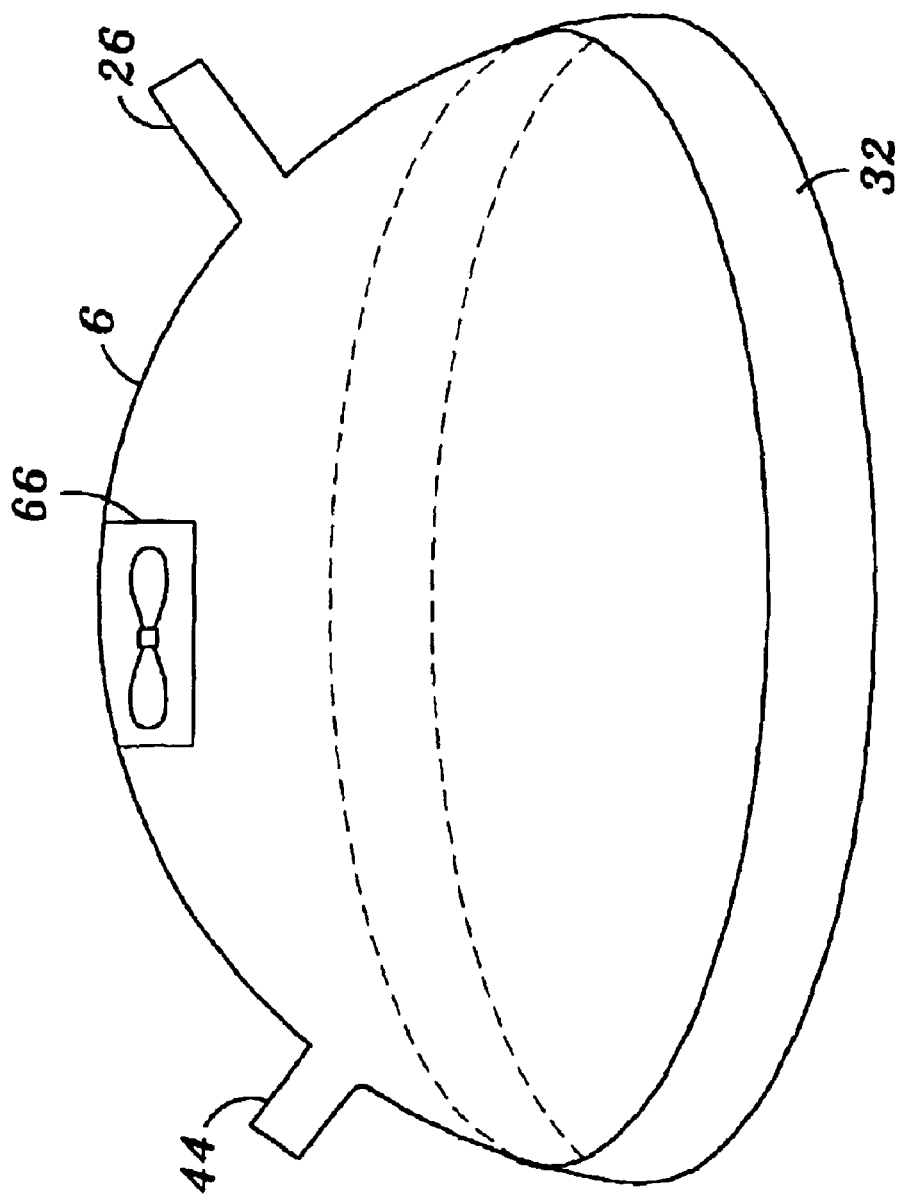
FIG. 4 illustrates a bathing unit including an agitator located therein.

FIG. 2 illustrates a bathing unit 6 in the shape of a boot that is used to treat an infected area 30 located on the leg of the patient 4. The bathing unit 6 includes an inflatable seal 61 that surrounds the leg region to make a substantially air-tight seal with the skin of the patient 4. This embodiment shows a nozzle 62 that is affixed near the inlet 26 of the bathing unit 6. The nozzle 62 directs a jet of NO gas onto the infected area 30. The jet of gaseous NO aids in penetrating the infected area 30 with NO to kill or inhibit the growth of pathogens. FIG. 3 shows another embodiment of the bathing unit 6 in the shape of a mitten or glove. The bathing unit 6 is also inflatable and contains an inflatable seal 61 that forms a substantially air-tight seal around the skin of the patient 4. FIG. 3 also shows an optional one way valve 64 located in the inlet 26. As seen in FIGS. 3 and 4, the inlet 26 and outlet 44 are located away from one another, and preferably on opposing sides of the treated area such that freshly delivered NO gas is not prematurely withdrawn from the bathing unit 6.

For treatment of an infected area 30, the bathing unit 6 is placed over the infected area 30. An air-tight seal is then formed between the skin of the patient 4 and the bathing unit 6. If the bathing unit 6 has an inflatable construction, the bathing unit 6 must be inflated with gas. Preferably, the bathing unit 6 is initially inflated only with the dilutent gas to prevent the leaking of NO and $NO_2$ from the device 2. Once an adequate air-tight seal has been established, the operator of the device initiates the flow of NO from the NO gas source 8 to the bathing unit 6. As described above, this may be accomplished manually or via the controller 36.

Once the bathing unit 6 has started to fill with NO gas, the vacuum unit 10 is turned on and adjusted to the appropriate output level. For an inflatable bathing unit 6, the output level (i.e., flow rate) of the vacuum unit 10 should be less than or equal to the flow rate of NO gas entering the bathing unit 6 to avoid deflating the bathing unit 6. In embodiments of the device where the bathing unit 6 is rigid, the vacuum unit 10 can be set to create a partial vacuum within the bathing unit 4. In this regard, the partial vacuum helps to form the air-tight seal between the skin of the patient 4 and the bathing unit 6. Of course, the vacuum unit 10 can also be set to withdraw gas at a substantially equal rate as the gas is delivered to the bathing unit 6. An effective amount of NO is delivered to the bathing unit 6 to kill pathogens and/or reduce the growth rate of the pathogens in the infected area 30. Pathogens include bacteria, viruses, and fungi.

FIG. 4 shows another embodiment of the invention in which the bathing unit 6 includes an agitator 66 that is used to create turbulent conditions inside the bathing unit 6. The agitator 66 preferably is a fan-type of mechanism but can include other means of creating turbulent conditions within the bathing unit 6. The agitator 66 aids in refreshing the infected area 30 with a fresh supply of NO gas.

While embodiments of the present invention have been shown and described, various modifications may be made without departing from the scope of the invention. The invention, therefore, should not be limited, except to the following claims, and their equivalents.

What is claimed:

1. A method of treating infected tissue with topical nitric oxide exposure comprising the steps of:
    providing a source of nitric oxide containing gas; and
    delivering the nitric oxide containing gas to a skin surface containing infected tissue so as to bathe the infected tissue with nitric oxide.
2. The method of claim 1, wherein the nitric oxide is delivered to the skin surface using a bathing unit surrounding the infected tissue.
3. The method of claim 1, wherein the concentration of nitric oxide in the nitric oxide containing gas that bathes the infected tissue is less than about 200 ppm.
4. The method of claim 1, further comprising the step of refreshing the infected tissue with a fresh supply of nitric oxide containing gas.
5. The method of claim 1, wherein a jet of nitric oxide containing gas is delivered to the portion of the skin surface containing the infected tissue.
6. The method of claim 1, wherein the source of nitric oxide containing gas is a pressurized cylinder containing nitric oxide gas.
7. The method of claim 1, further comprising the step of monitoring the concentration of nitric oxide bathing the infected tissue.
8. The method of claim 1, further comprising the step of monitoring the concentration of nitrogen dioxide bathing the infected tissue.
9. The method of claim 1, further comprising the step of evacuating the nitric oxide containing gas from the area surrounding the infected tissue.
10. A method of treating infected tissue with topical nitric oxide exposure comprising the steps of:
    providing a source of nitric oxide containing gas;
    delivering the nitric oxide containing gas to a skin surface containing infected tissue so as to bathe the infected tissue with nitric oxide;
    evacuating the nitric oxide containing gas from the area surrounding the infected tissue; and
    stripping nitric oxide from the evacuated gas.
11. A method of treating infected tissue with topical nitric oxide exposure comprising the steps of:
    providing a source of nitric oxide containing gas;
    delivering the nitric oxide containing gas to a skin surface containing infected tissue so as to bathe the infected tissue with nitric oxide;
    evacuating the nitric oxide containing gas from the area surrounding the infected tissue; and
    stripping a nitric dioxide from the evacuated gas.
12. The method of claim 4, wherein the step of refreshing utilizes an agitator.
13. A method of treating infected skin tissue comprising the steps of:
    identifying the infected skin tissue of a human;
    providing a flow-controlled source of nitric oxide gas; and
    delivering the nitric oxide gas to at least a portion of the infected skin tissue.
14. The method of claim 13 further comprising the step of sealing the nitric oxide gas to prevent contact with air in the atmosphere.
15. The method of claim 13 further comprising the step of diluting the nitric oxide gas with an inert gas.
16. The method of claim 13 wherein the flow-controlled source of nitric oxide gas flows from a pressurized cylinder containing nitric oxide gas.
17. The method of claim 16 further comprising the step of reducing pressure of the nitric oxide gas before delivering the nitric oxide gas to the infected skin tissue.
18. The method of claim 13 further comprising evacuating the nitric oxide gas at a flow rate substantially equal to a flow rate of the nitric oxide gas delivered to the infected skin tissue.
19. A method of treating infected skin tissue with topical exposure to nitric oxide gas comprising the steps of:
    providing a source of nitric oxide gas;
    diluting the nitric oxide gas with an inert gas;
    delivering the diluted nitric oxide gas to at least a portion of the infected skin tissue.
20. The method of claim 19 wherein the step of diluting the nitric oxide gas is performed through a gas blender.
21. The method of claim 19 wherein the nitric oxide gas delivered to the skin is flow controlled.
22. The method of claim 19 wherein the step of diluting the nitric oxide gas further comprises the step of delivering the inert gas to an air-tight sealed area over the infected skin tissue.
23. The method of claim 19 further comprising the step of monitoring the concentration of nitric oxide being delivered.

* * * * *